(12) United States Patent
Shah

(10) Patent No.: US 8,920,720 B2
(45) Date of Patent: Dec. 30, 2014

(54) ROTARY TISSUE PROCESSOR WITH CONFIGURABLE STATIONS

(75) Inventor: Preyas Shah, Warminster, PA (US)

(73) Assignee: Rushabh Instruments, Inc., Warrington, PA (US)

( * ) Notice: Subject to any disclaimer, the term of this patent is extended or adjusted under 35 U.S.C. 154(b) by 620 days.

(21) Appl. No.: 13/152,387

(22) Filed: Jun. 3, 2011

(65) Prior Publication Data

US 2012/0310401 A1    Dec. 6, 2012

(51) Int. Cl.
 *G01N 1/30* (2006.01)
 *G01N 35/04* (2006.01)
 *G01N 1/31* (2006.01)

(52) U.S. Cl.
 CPC ............... *G01N 1/312* (2013.01); *G01N 35/04* (2013.01); *G01N 2035/0441* (2013.01)
 USPC .......................................... 422/64; 422/536

(58) Field of Classification Search
 USPC .............................................. 422/63–67, 536
 See application file for complete search history.

(56) References Cited

U.S. PATENT DOCUMENTS

| | | | | |
|---|---|---|---|---|
| 3,762,362 | A | * | 10/1973 | Lipshaw ................. 118/666 |
| 4,141,312 | A | | 2/1979 | Louder |
| 4,688,517 | A | | 8/1987 | Hollman |
| 4,834,019 | A | | 5/1989 | Gordon |
| 5,147,551 | A | * | 9/1992 | Averette ................. 210/640 |
| 5,895,628 | A | | 4/1999 | Heid |
| 6,080,365 | A | * | 6/2000 | Thiem et al. ............ 422/537 |
| 6,444,170 | B1 | | 9/2002 | Heid et al. |
| 7,083,761 | B2 | | 8/2006 | Zimmermann |
| 7,371,346 | B2 | | 5/2008 | Windeyer |
| 2001/0000487 | A1 | * | 4/2001 | Essenfeld et al. ........... 435/40.5 |
| 2005/0118670 | A1 | | 6/2005 | Lihl et al. |
| 2006/0127280 | A1 | | 6/2006 | Zimmermann |
| 2007/0243626 | A1 | | 10/2007 | Windeyer |
| 2010/0216222 | A1 | | 8/2010 | Ulbrich |

FOREIGN PATENT DOCUMENTS

| | | |
|---|---|---|
| DE | 101 28 126 A1 | 12/2002 |
| DE | 10128126 A1 | 12/2002 |
| EP | 0 077 477 | 4/1983 |
| EP | 0077477 A1 | 4/1983 |
| GB | 2 319 608 A | 5/1998 |
| GB | 2319608 A | 5/1998 |

OTHER PUBLICATIONS

International Search Report, dated Aug. 30, 2012, corresponding to PCT/US2012/039955, filed May 30, 2012.
International Preliminary Report on Patentability, dated Dec. 4, 2013, corresponding to International Application No. PCT/US2012/039955, filed May 30, 2012.

* cited by examiner

*Primary Examiner* — Jill Warden
(74) *Attorney, Agent, or Firm* — RatnerPrestia

(57) ABSTRACT

A configurable tissue processing system is disclosed that includes a plurality of configurable tissue processing stations, each station configured to receive tissue samples and selectively configurable to heat, agitate and apply either a positive pressure or a vacuum pressure to the received tissue samples; a transport mechanism that is configured to transport the tissue samples between the plurality of configurable tissue processing stations; and a control unit coupled to the plurality of configurable tissue processing stations and to the transport mechanism, the control unit controlling the transport mechanism to selectively position the tissue samples in the plurality of configurable tissue processing stations, and the control unit configuring each of the plurality of configurable tissue processing stations to heat, agitate and apply either a positive pressure or a vacuum pressure to the received samples. Also disclosed is a method of configuring the plurality of tissue processing stations.

22 Claims, 13 Drawing Sheets

ROTARY TISSUE PROCESSOR WITH CONFIGURABLE STATIONS

FIELD OF THE INVENTION

The invention is generally directed to a tissue processor and the field of histology.

BACKGROUND OF THE INVENTION

A typical tissue processor automatically performs fixation, dehydration, clearing, and paraffin impregnation of tissue samples (e.g., liver tissue, breast tissue, prostate tissue, etc.). A station-type processor includes a plurality of stations for processing the tissue samples, which are contained within individual cassettes. The tissue cassettes are loaded into a single basket and taken from one station to the next station for processing. An example of a station processor is disclosed in U.S. Pat. No. 6,080,365 to Thiem et al., which is incorporated fully herein by reference. The stations of such processors perform dedicated tasks such as fixation, dehydration, clearing, and paraffin impregnation.

SUMMARY OF THE INVENTION

According to one aspect of the invention, a configurable tissue processing system is provided. The configurable tissue processing system includes a plurality of configurable tissue processing stations, whereby each station is configured to receive one or more tissue samples and selectively configurable to heat, agitate and apply a pressure to the received tissue samples. The pressure may be a positive pressure or a vacuum pressure. A transport mechanism is configured to transport the one or more tissue samples between the plurality of configurable tissue processing stations. A control unit is coupled to the plurality of configurable tissue processing stations and to the transport mechanism. The control unit controls the transport mechanism to selectively position the one or more tissue samples in the plurality of configurable tissue processing stations. The control unit also configures each of the plurality of configurable tissue processing stations to heat, agitate and apply either a positive pressure or a vacuum pressure to the received samples.

In one embodiment, each tissue sample is loaded in a cassette, multiple cassettes are loaded onto a tray, and multiple trays are loaded onto a carrier. The configurable tissue processing system includes multiple carriers. Each carrier is moved between the various processing stations. All of the tissue samples that are contained within a single carrier are simultaneously processed the same way at a tissue processing station, however, the individual carriers may be processed differently.

According to another aspect of the invention, a configurable tissue processing system includes a plurality of configurable tissue processing stations, whereby each station is configured to receive one or more tissue samples. A transport mechanism is configured to transport the one or more tissue samples between the plurality of configurable tissue processing stations. A pressure delivery system selectively exposes the one or more tissue samples at every tissue processing station to either a positive pressure or a vacuum pressure.

According to yet another aspect of the invention, a method for configuring a plurality of tissue processing stations of a tissue processing system is provided. The method includes the steps of receiving parameters to individually configure each of the plurality of tissue processing stations to heat, agitate and apply either a positive pressure or a vacuum pressure to tissue samples that are positioned at the plurality of tissue processing stations; and configuring each of the plurality of tissue processing stations to heat, agitate, and apply either a positive pressure or a vacuum pressure during processing at each processing station in accordance with the received parameters.

According to another aspect of the invention, each tissue processing station may be configured to perform a variety of different processing sequences. For example, a first program for a particular station may heat, agitate and apply a pressure to a sample docked at that station for a first predetermined time, whereas another program for that station may only heat and agitate a sample docked at that station for a second predetermined time that is different from the first predetermined time.

According to yet another aspect of the invention, different processing programs (i.e., different temperature, pressure and agitation selections) can be executed simultaneously so as long as the processing time at each station is the same in a given program and is the same for all of the programs that are running simultaneously.

BRIEF DESCRIPTION OF THE DRAWING FIGURES

Figure 9:
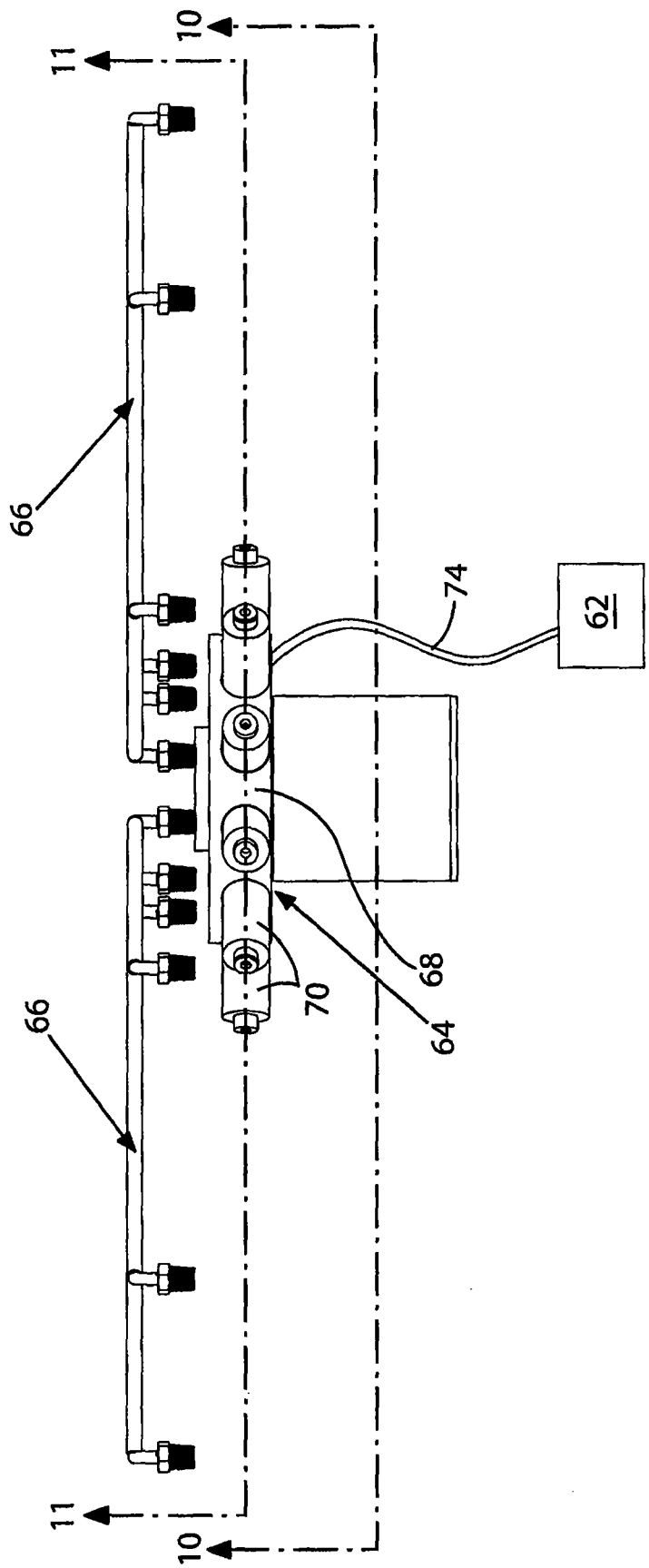
Figure 10:
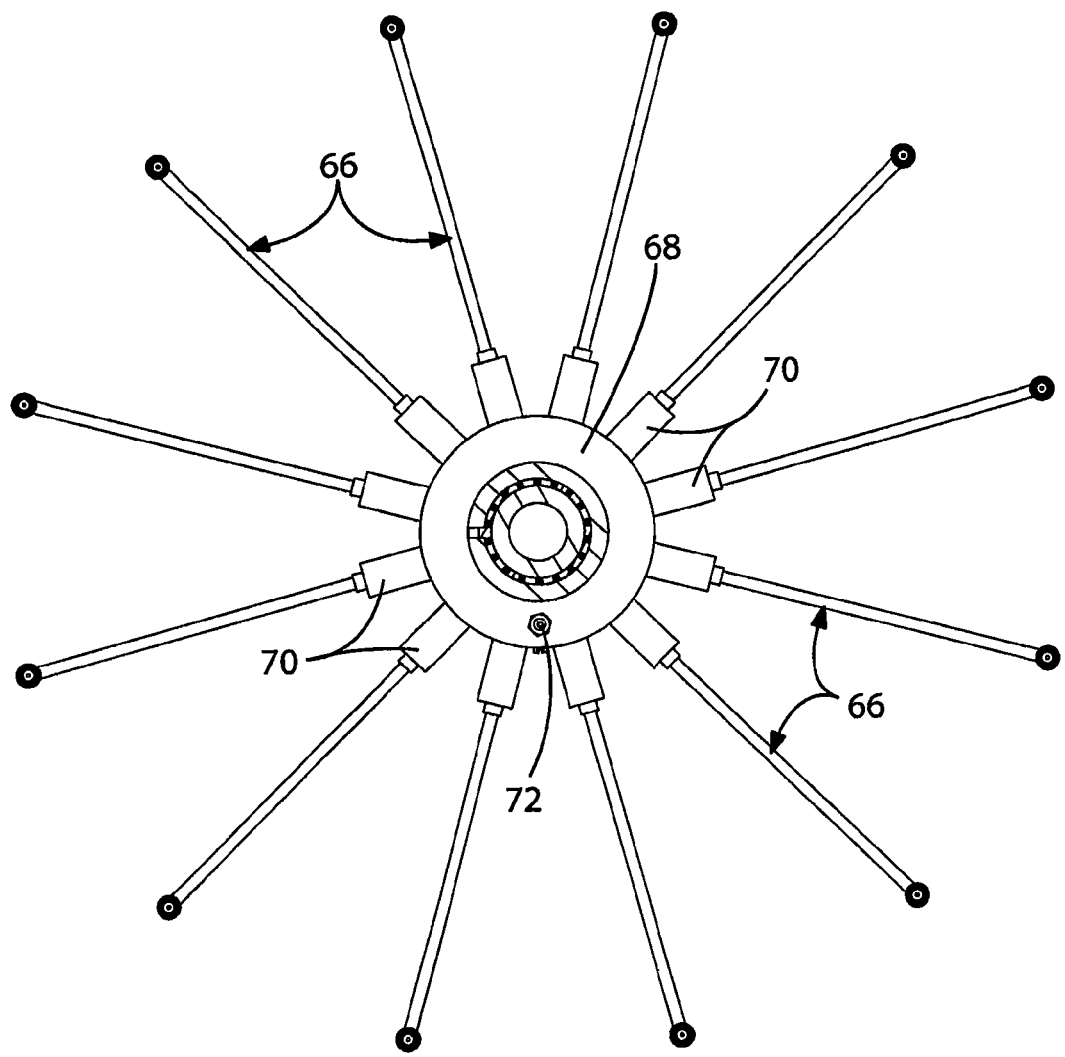
Figure 11:
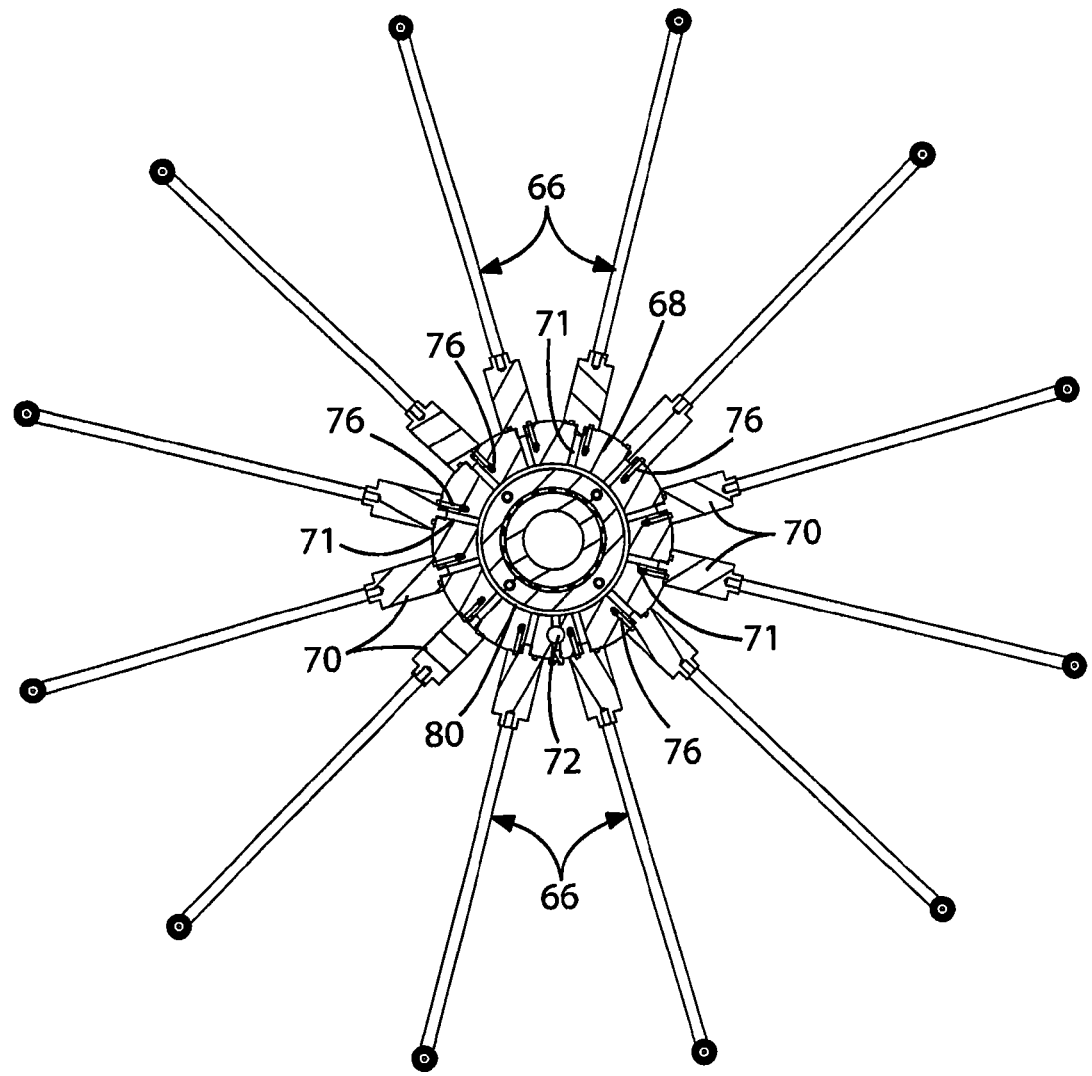

FIGS. 10 and 11 depict cross-sectional views of the pressure delivery system of FIG. 9 taken along the lines 10-10 and 11-11, respectively.

Figure 1:
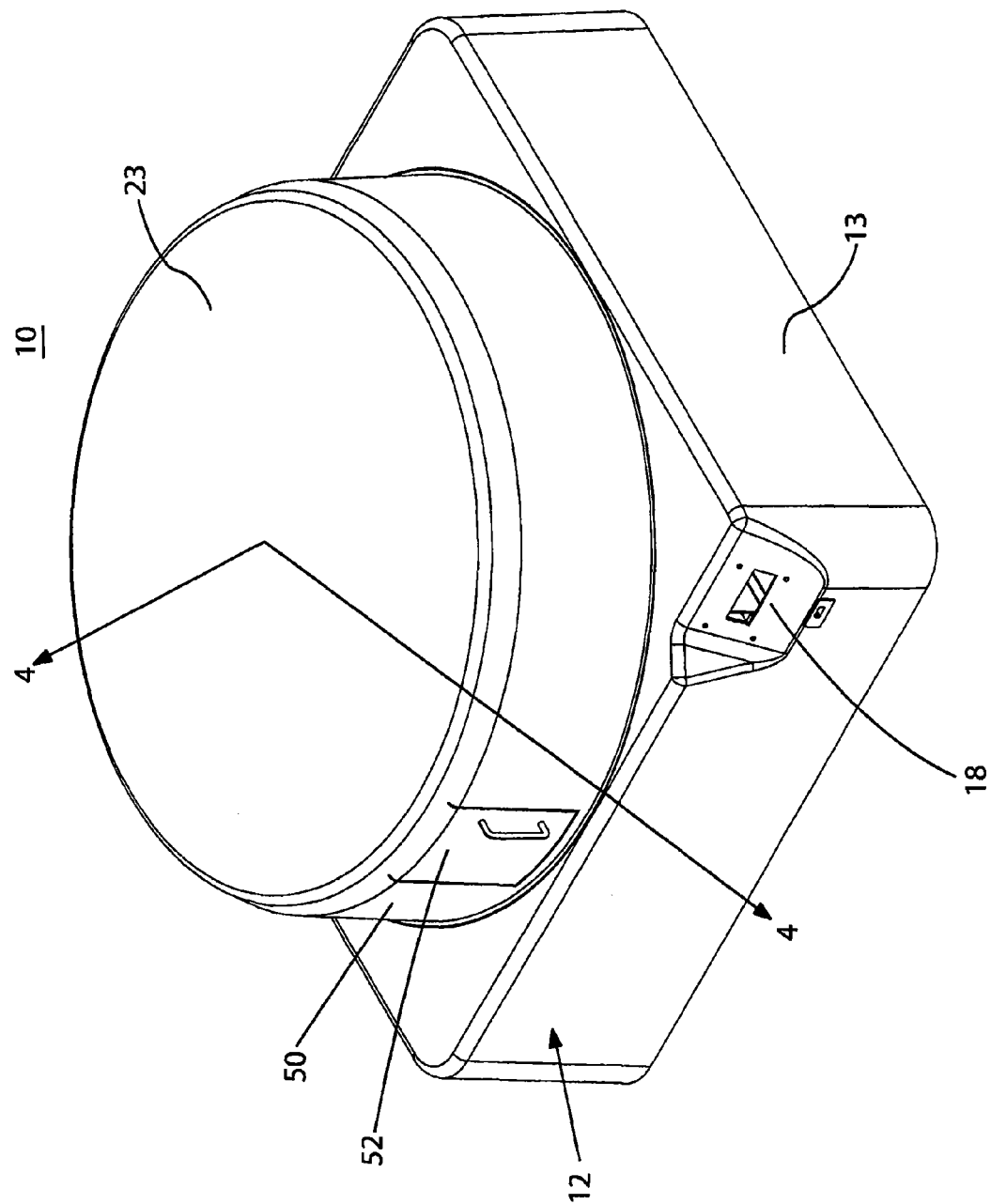
FIG. 1 depicts a perspective view of a rotary tissue processor with configurable tissue processing stations, according to an exemplary embodiment of the invention.
Figure 12:
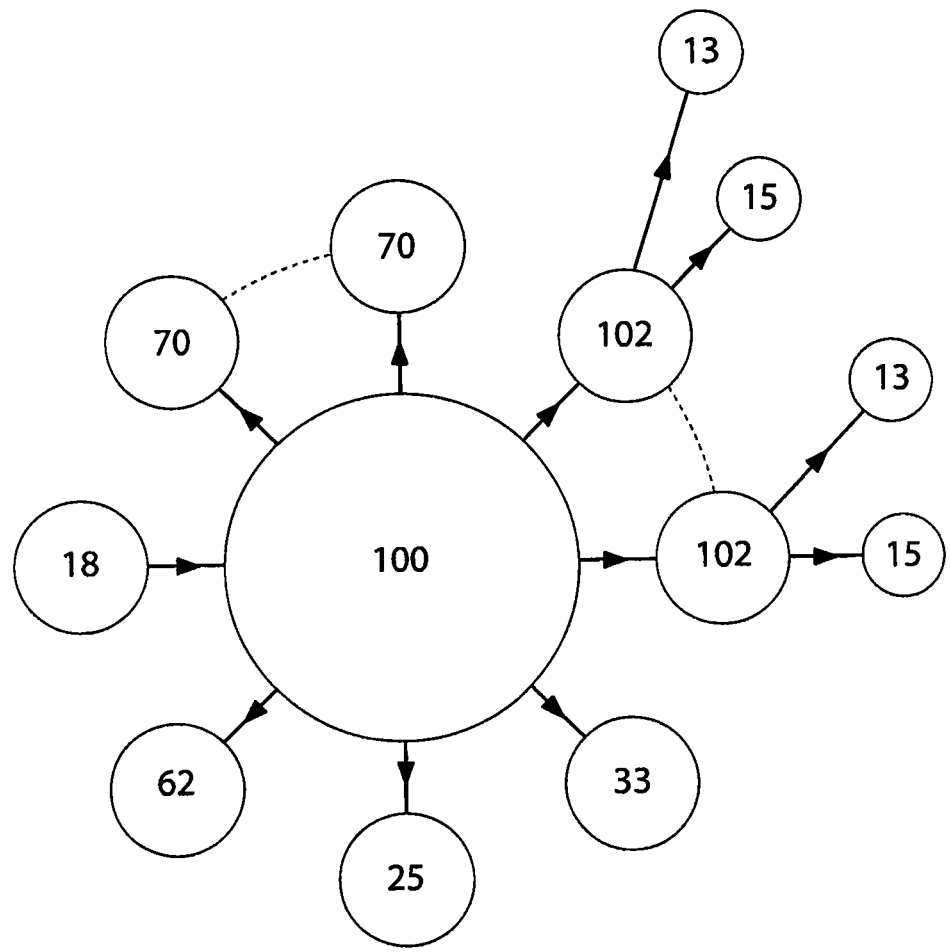

FIG. 12 depicts a simplified electrical schematic diagram of the rotary tissue processor of FIG. 1.

Figure 13:
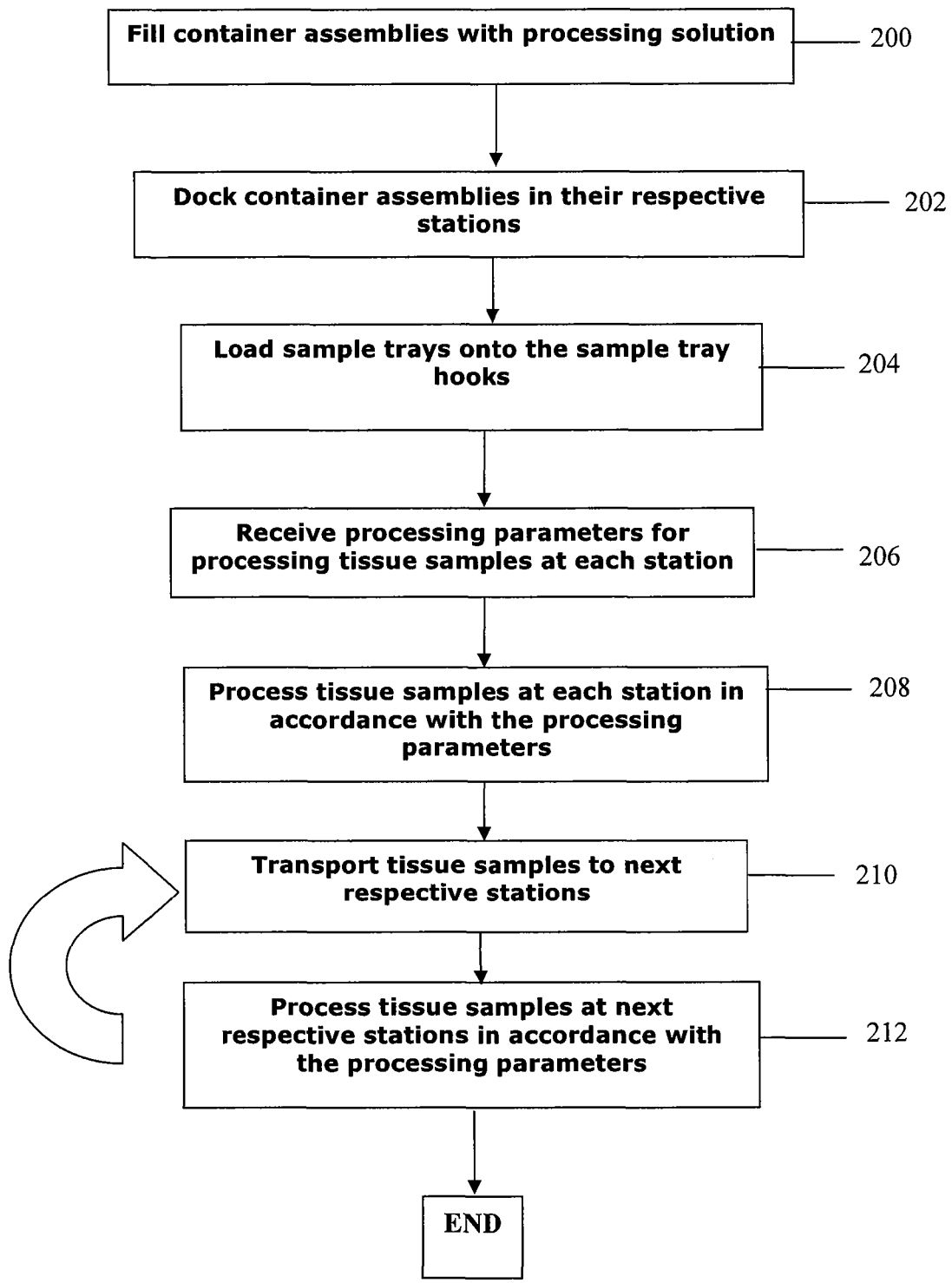

FIG. 13 depicts a schematic block diagram of an exemplary method of operating a rotary tissue processor.

DETAILED DESCRIPTION OF THE DRAWING FIGURES

FIGS. 1-5 depict a rotary tissue processor 10 having configurable tissue processing stations, according to an exemplary embodiment of the invention. The tissue processor 10 generally includes a base assembly 12 including twelve tissue processing stations 14 and a transport mechanism 16 that is configured to rotate about axis 'A' and translate along axis 'A' to move one or more tissue sample carriers 20 between adjacent tissue processing stations 14.

The twelve tissue processing stations 14 are radially positioned around the center of the processor 10. Each tissue processing station 14 is configured to process a carrier 20 filled with one or more tissue samples that is positioned within the interior region of a container assembly 15 sized to receive one or more samples. Each tissue sample may be inserted into a cassette that is loaded into a tray, which is then loaded into a carrier 20. For example, multiple trays may be loaded onto each carrier 20, multiple tissue cassettes may be loaded onto each tray, and each tissue cassette may contain one or more tissue samples.

Each tissue processing station 14 generally includes a dedicated container assembly 15 that is releasably mounted in a container receiving area 17 of the base assembly 12, a motor-driven magnet 13 (see FIG. 4) positioned beneath the container assembly 15, and a station controller (not shown) for controlling the operation of the station 14. It should be understood that the number of tissue processing stations 14, tissue processing container assemblies 15 and container receiving areas 17 may vary from that which is shown and described.

Figure 6:
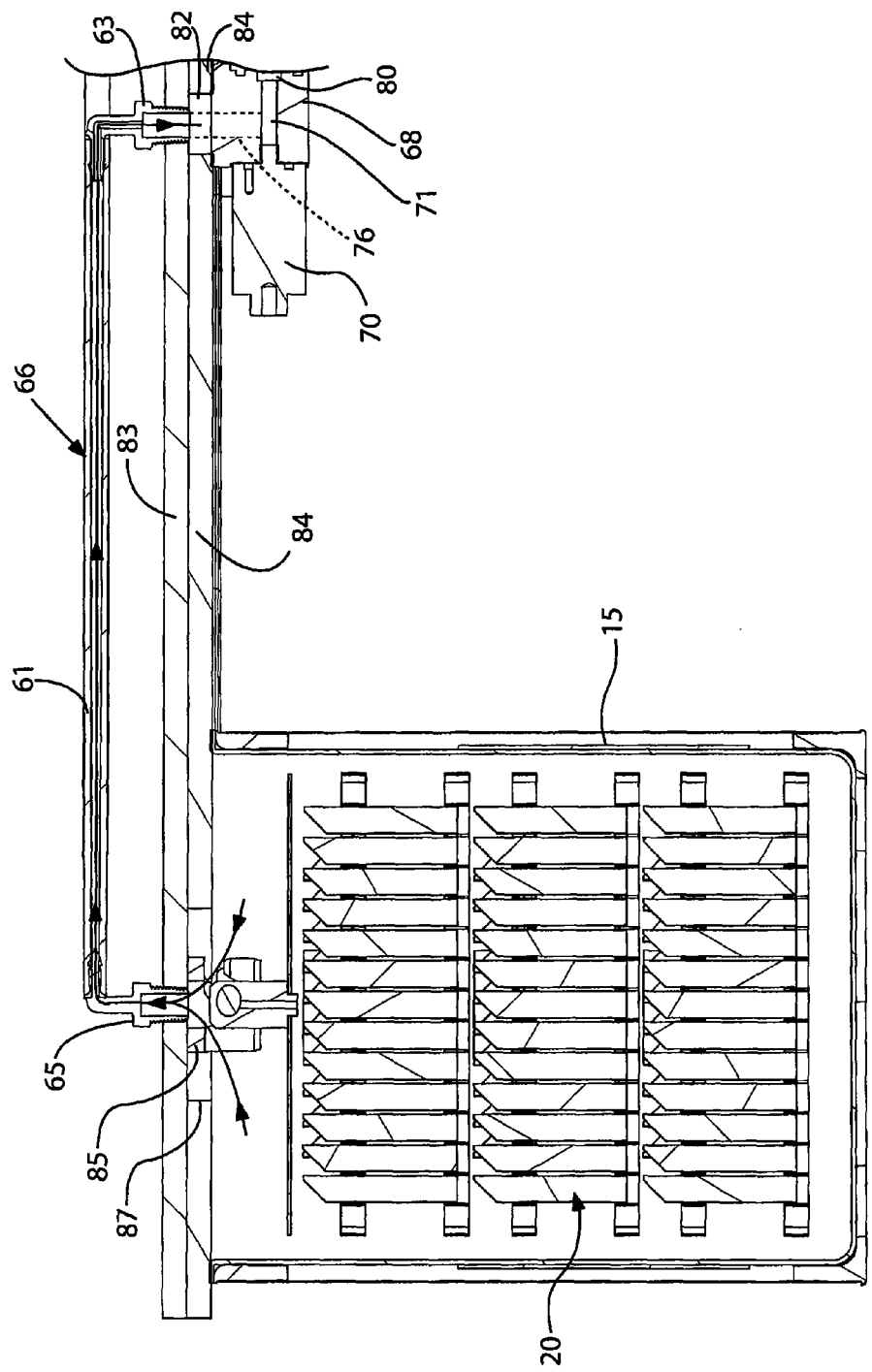
FIG. 6 is a detailed view of the rotary tissue processor of FIG. 4 which depicts a pressure delivery passageway for one container.
Figure 7:
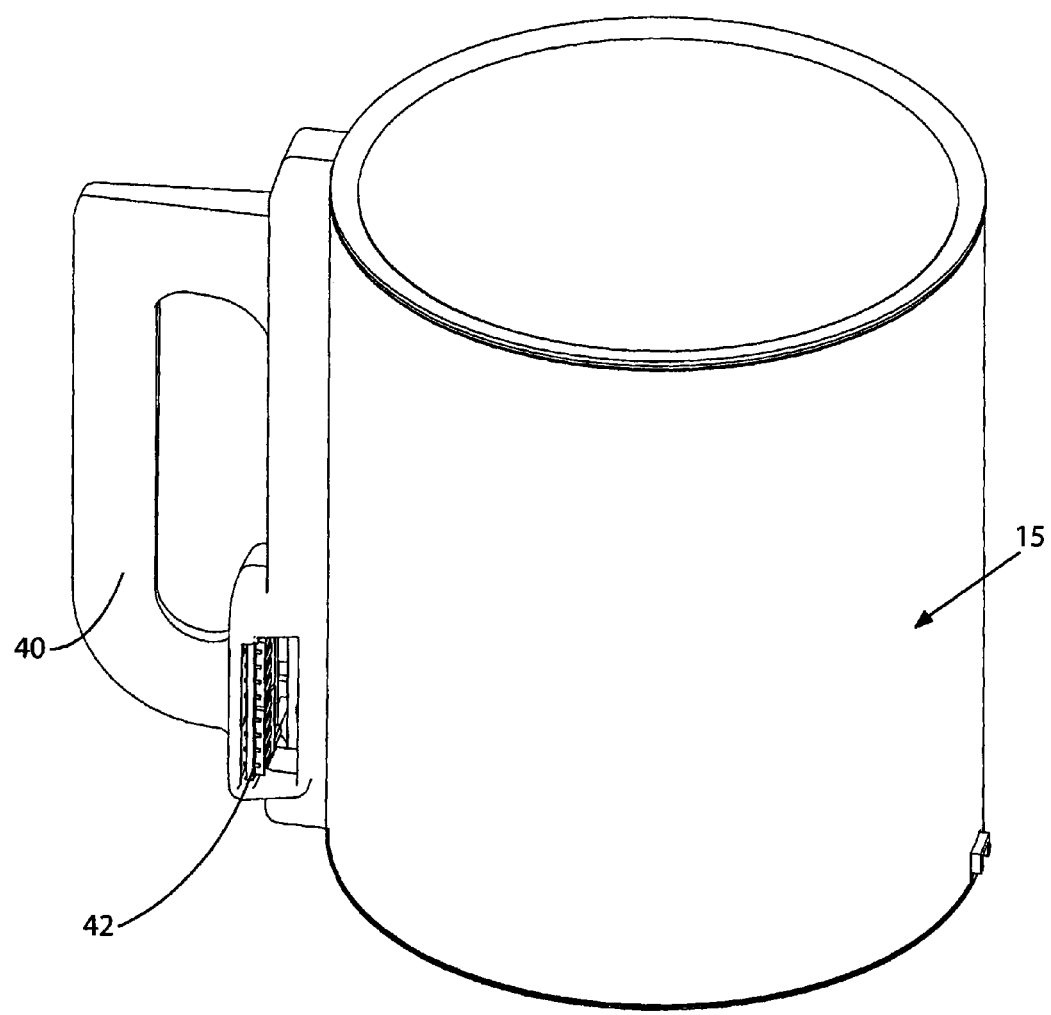
FIG. 7 depicts a perspective view of a container assembly of the rotary tissue processor of FIG. 1.
Figure 8:
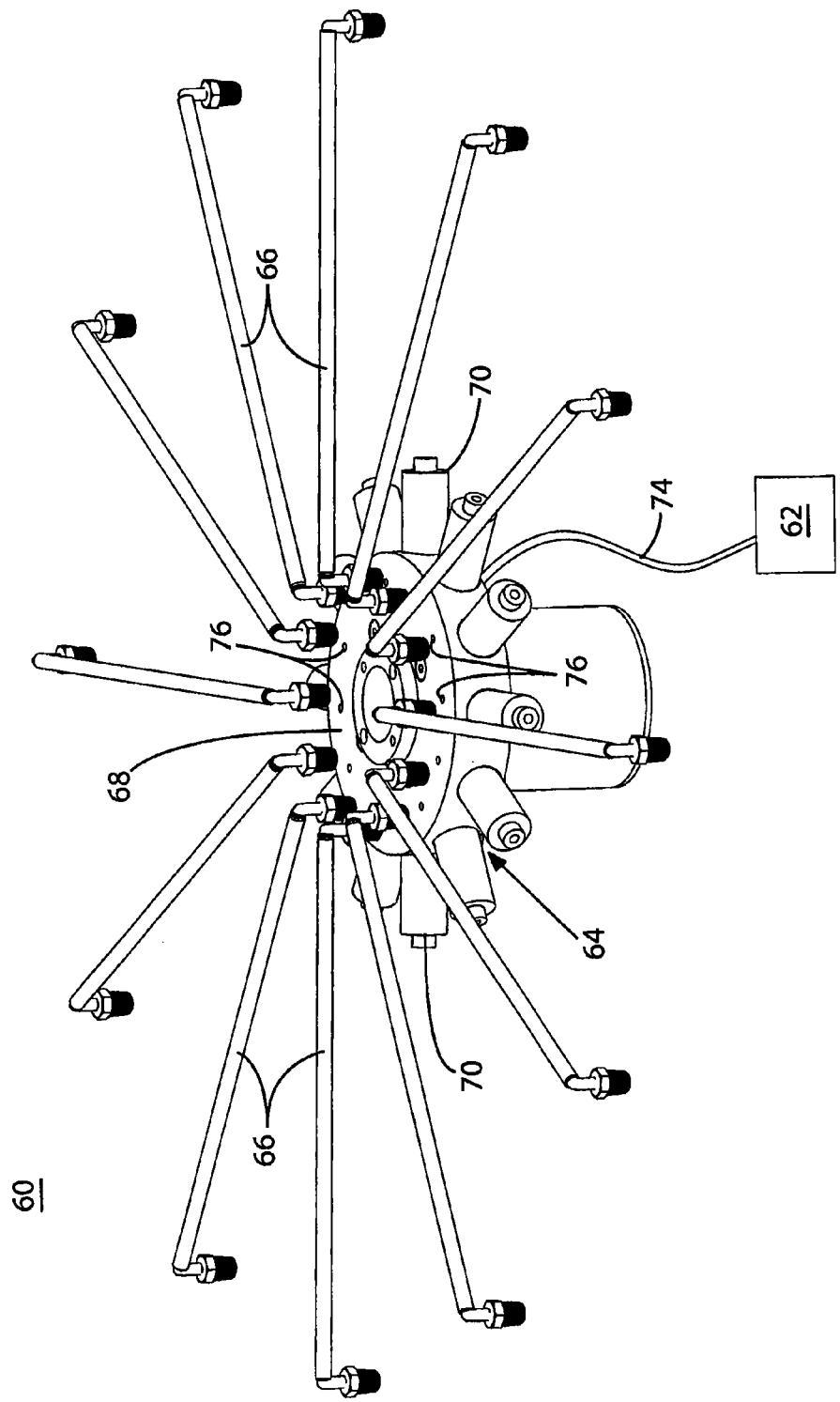
FIGS. 8 and 9 depict a perspective view and a side elevation view, respectively, of a pressure delivery system of the rotary tissue processor of FIG. 1.

FIG. 7 depicts a detailed view of a container assembly 15. According to one aspect of the invention, every container assembly 15 of the rotary processor 10 is the same. Each container assembly 15 includes a double-walled container defining a hollow interior region for containing a carrier 20 of tissue samples and processing solution (see FIG. 6). The container assembly 15 includes a handle 40 for grasping the container assembly 15. The electrical connector 42 is mounted to the body of the container 15. Although not explicitly shown, a heating element that receives current from the electrical connector 42 is positioned between the walls of each container assembly 15. The heating element of each container assembly 15 heats the processing solution that is contained within a container assembly 15, thus heating the tissue samples that are immersed in that processing solution. The heating element may be a sleeve that is positioned between the walls of the double-walled container or individual heating elements that are mounted to a wall of the container. Although not shown, each container assembly 15 may also include a temperature sensor for measuring the temperature of the container assembly 15.

Figure 2:
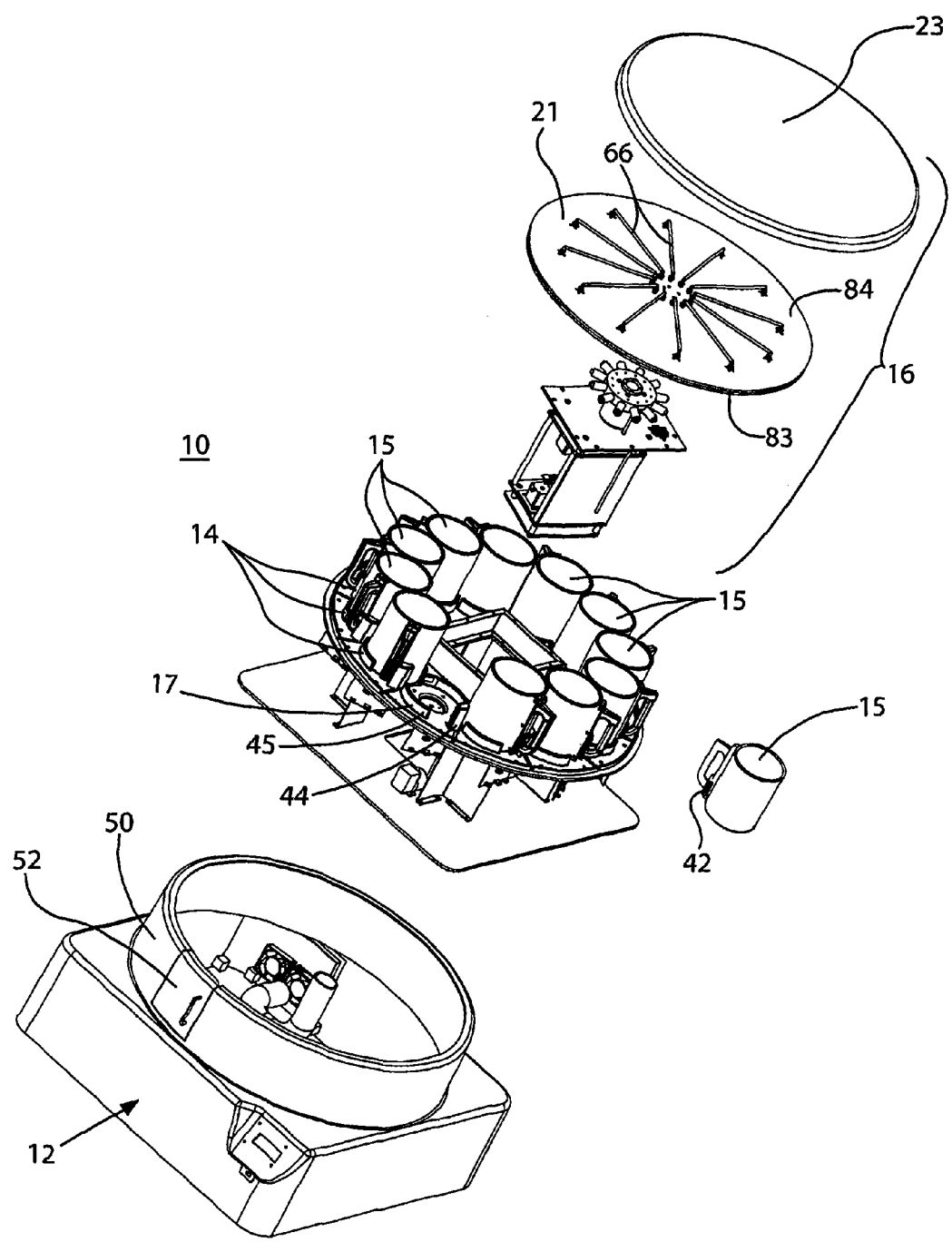
FIGS. 2 and 3 depict exploded views of the rotary tissue processor of FIG. 1.

As best shown in FIG. 2, each container assembly 15 is releasable mounted in a respective container receiving area 17 of the base assembly 12. Each container receiving area 17 includes an electrical connector 44 for releasably mating with the electrical connector 42 of a respective container assembly 15, a vertically extending semi-cylindrical wall 45, and a slot defined between the wall 45 and the connector 44. The wall 45 defines a recess in which the bottom end of a container assembly 15 is seated. The aforementioned slot provides clearance for mating the connectors 42 and 44 together. To dock a container assembly 15 into a station 14, the bottom end of the container assembly 15 is seated in the recess that is defined by the wall 45. The handle 40 of the container assembly 15 is then rotated within the slot that is defined between the wall 45 and the connector 44 until the connector 42 of the container assembly 12 is sufficiently mated with the connector 44 of the station 14.

Figure 3:
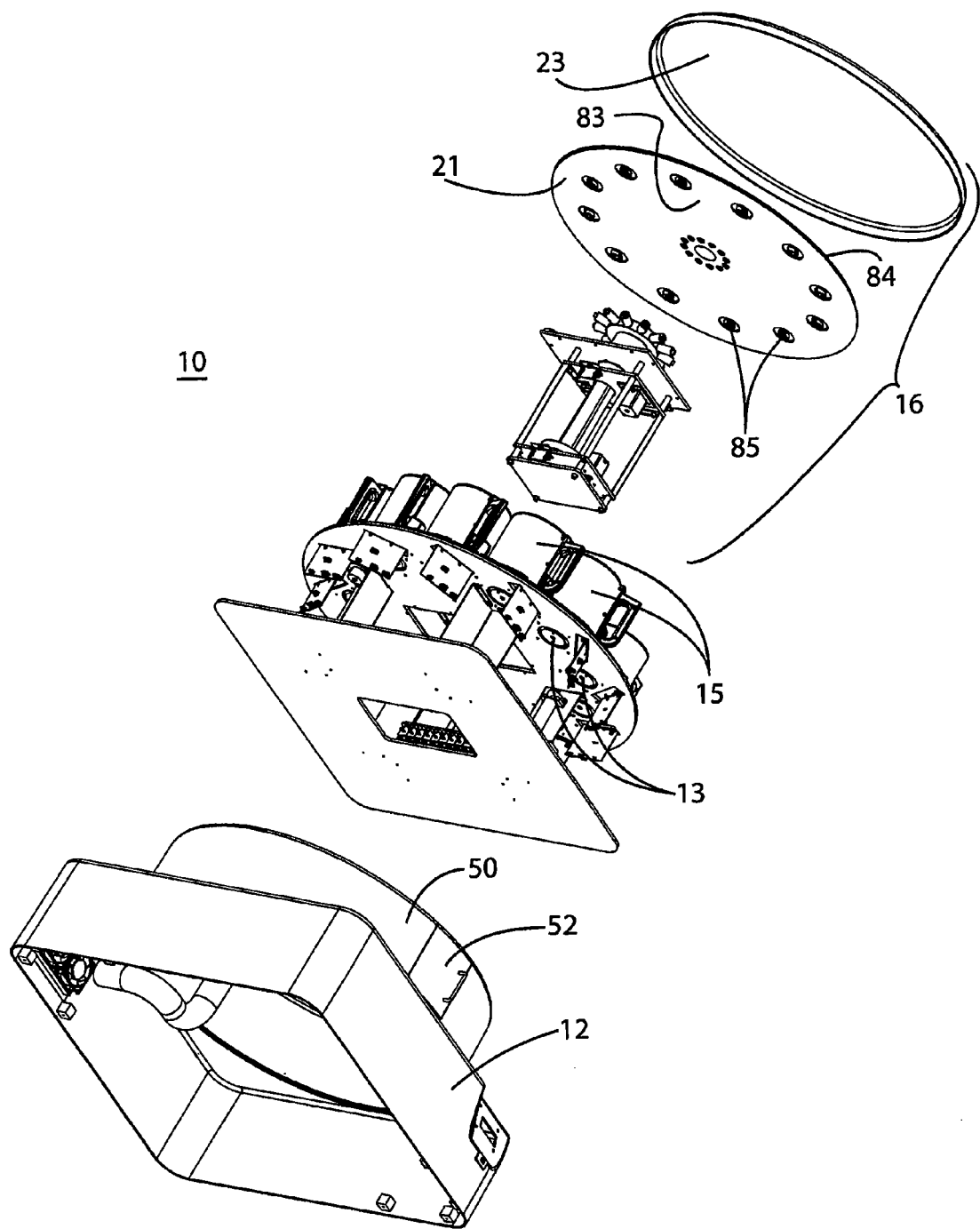

Referring now to FIGS. 1-3, the container assemblies 15 are removable from rotary processor 10 such that they can be manually filled or refilled with a processing solution. A fume shield 50 is rotatably mounted to the top end of the base assembly 12 to limit or prevent the inadvertent egress of fumes from the processor 10. One or more fans (see FIG. 4) are provided on the processor 10 to exhaust the fumes.

Rotation of the fume shield 50 may be manual or automated. The fume shield 50 includes an access door 52 through which a container assembly 15 is removed. To remove a particular container assembly 15 from the processor 10, the fume shield 50 is rotated until the access door 52 is aligned with that container assembly 15. The access door 52 is opened and the container assembly 15 is removed from its container receiving area 17 by disconnecting the connectors 42 and 44. The container assembly 15 may be filled or refilled with solution and mounted into its container receiving area 17.

Figure 4:
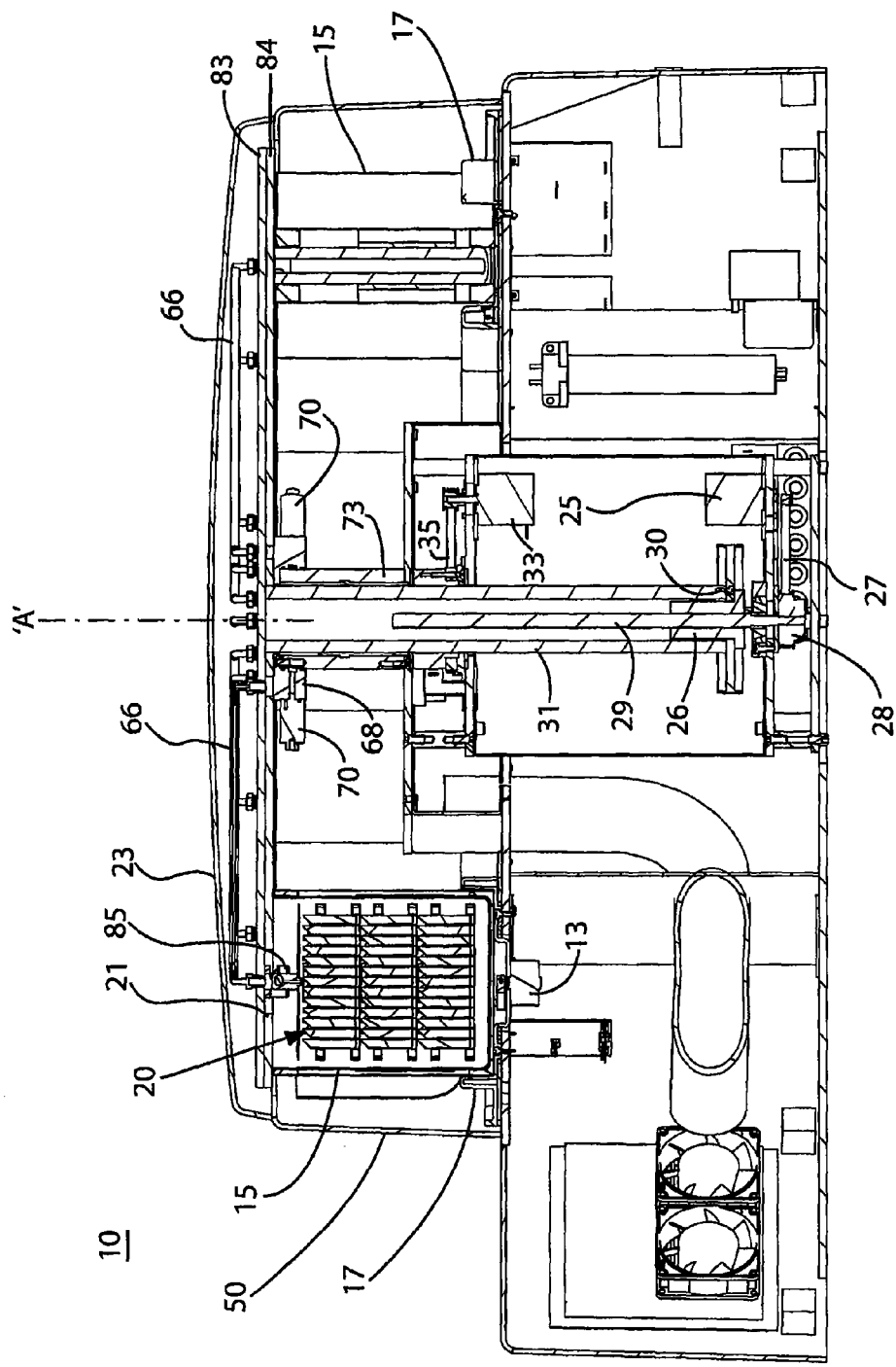
FIG. 4 depicts a cross-sectional view of the rotary tissue processor of FIG. 1 taken along the lines 4-4.
Figure 5:
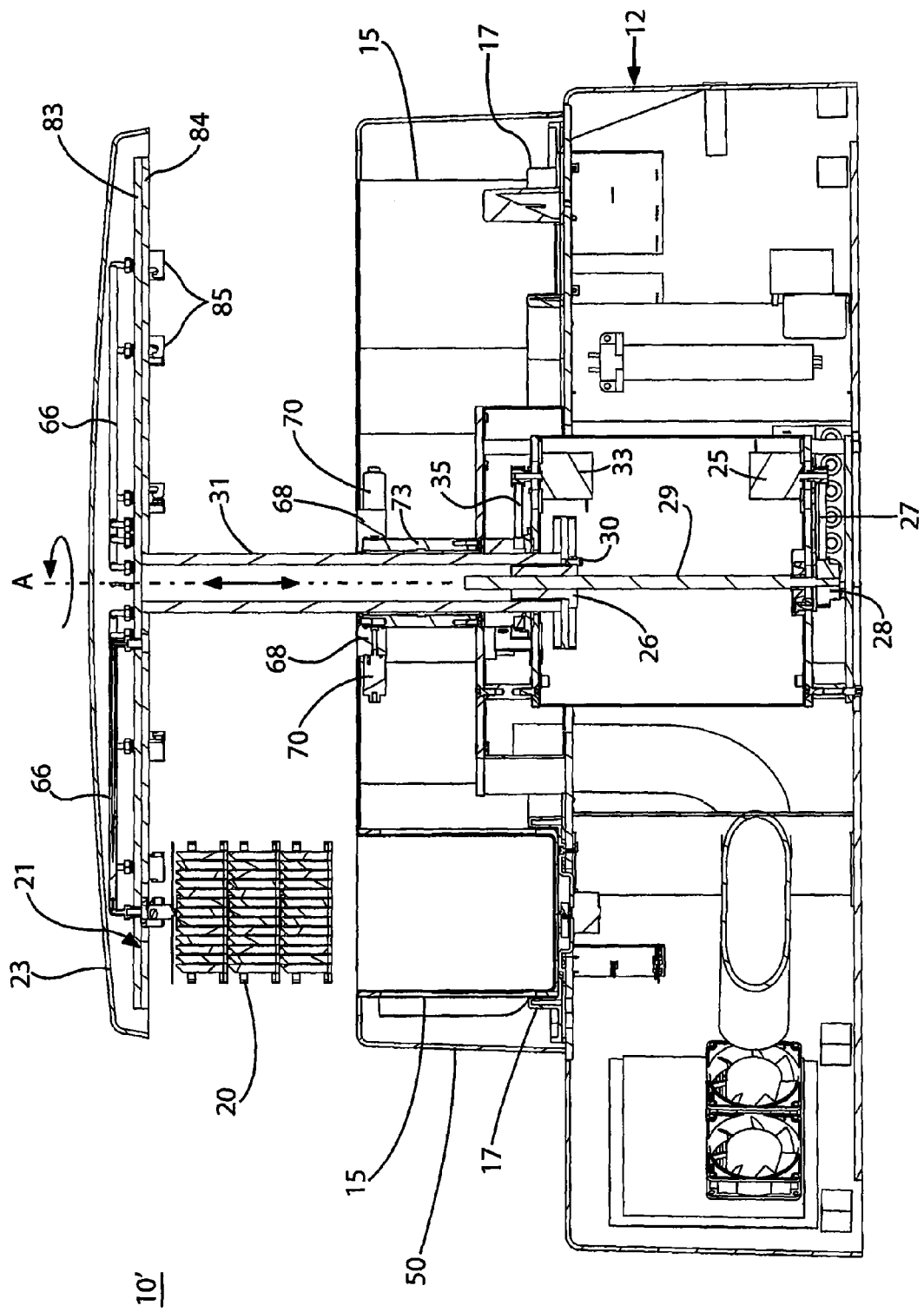
FIG. 5 depicts a cross-sectional view of the rotary tissue processor of FIG. 1 taken along the lines 4-4, however, the transport mechanism of the rotary tissue processor is shown in a raised position.

Referring now to FIGS. 4-6, the transport mechanism 16 of the rotary processor 10 is configured to sequentially transport the sample carriers 20 between adjacent stations 14. It should be understood that, in operation, the sample carriers 20 move from one container assembly 15 to another. In the illustrated embodiment, the container assemblies 15 are dedicated to individual stations 14 and do not move.

The transport mechanism 16 generally includes a carrier assembly 21 for carrying tissue sample carriers 20, means for translating the carrier assembly 21, and means for rotating the carrier assembly 21. The means for translating the carrier assembly 21 along the axis 'A' includes a motor 25 having a rotatable output shaft, a drive belt 27 that is engaged with the output shaft of the motor 25 and a gear 28 that is fixedly mounted to the bottom of the end threaded shaft 29. A threaded nut 26 is threadedly engaged with the threaded shaft 29 such that the threaded nut 26 can rotate along the surface of the threaded shaft 29. The threaded nut 26 is fixedly engaged to a vertical post 31 by a fastener 30. The carrier assembly 21 is fixedly mounted to the top end of the vertical post 31.

In operation, rotation of the output shaft of the motor 25 rotates the drive belt 27 which rotates the threaded shaft 29 which translates the threaded nut 26 along the axis 'A.' Because the vertical post 31 and the carrier assembly 21 are fixedly mounted to the threaded nut 26, those components are also translated along the axis 'A.' The rotational direction of the output shaft of the motor 25 determines the translational direction of the carrier assembly 21 along axis 'A.' Those of ordinary skill in the art will readily recognize other apparatuses for translating a carrier assembly from the description herein.

The means for rotating the carrier assembly 21 about the axis 'A' includes a motor 33 having a rotatable output shaft, and a drive belt 35 that is engaged with the output shaft of the motor 33 and the exterior surface of the vertical post 31. In operation, rotation of the output shaft of the motor 33 rotates the drive belt 35 which rotates the vertical post 31 and the carrier assembly 21, which is mounted to the vertical post 31, about the axis 'A.' The rotational direction of the output shaft of the motor 33 influences the rotational direction of the carrier assembly 21 about axis 'A.' Those of ordinary skill in the art will readily recognize other apparatuses for rotating a carrier assembly from the description herein.

The carrier assembly 21 includes the vertical post 31, an exterior cover 23 and two plates 83 and 84 that are all fixedly mounted, either directly or indirectly, to the vertical post 31. The cover 23, the plates 83 and 84 and the vertical post 31 of the carrier assembly 21 are mounted together such that they form a subassembly. The container assemblies 15 remain fixed in position while the carrier assembly 21 rotates and translates thereabove.

The cover 23 substantially encases the base assembly 12 of the rotary processor 10 when the carrier assembly 21 is in the lowered position that is shown in FIG. 4. The plates 83 and 84, which are sandwiched together, are mounted beneath the cover 23. As best shown in FIGS. 5 and 6, twelve clips 85 are fixedly mounted to the underside of the plate 83, and each clip 85 is configured to releasably hold a sample carrier 20. The sample carriers 20 rotate and translate along with the vertical post 31 because the sample carriers 20 are mounted to the clips 85; the clips 85 are mounted to the underside of the plate 83; and the plate 83 is mounted to the vertical post 31.

Twelve conduit assemblies 66 are also mounted to the plate 83 of the carrier assembly 21. The conduit assemblies 66 also form part of a pressure delivery system 60 of the rotary processor 10 which is described hereinafter. Like the clips 85, the conduit assemblies 66 rotate and translate along with the vertical post 31. Each conduit assembly 66 generally includes a hollow tube 61 that extends between and interconnects an inlet connector 63 and an outlet connector 65. The tube 61 is positioned at an elevation above the top plate 83. The connectors 63 and 65 are fixed to and positioned through holes that are disposed in the top plate 83. An opening 82 is provided in the lower plate 84 adjacent each inlet connector 63 to permit fluid communication between the inlet connectors 63 and a solenoid valve assembly 64 of a pressure delivery system 60, the purpose of which will be described later. The inlet connectors 63 are not physically connected to the solenoid valve assembly 64. An opening 85 is provided in the lower plate 84 adjacent each outlet connector 65 to permit fluid communication between the inlet connectors 65 and the container assemblies 15, the purpose of which is described below. The outlet connectors 65 are not physically connected to their respective container assemblies 15.

FIGS. 8-11 depict a pressure delivery system 60 of the rotary processor 10 that is configured to deliver either vacuum or positive pressure to the individual container assemblies 15. The system 60 generally includes a vacuum pump 62 (shown schematically) for producing vacuum and/or positive pressure, a solenoid valve assembly 64 that is fluidly connected to the vacuum pump 62, and twelve conduit assemblies 66 that fluidly connect the solenoid valve assembly 64 with the container assemblies 15 to deliver either vacuum or positive pressure to those container assemblies 15. Fluidly connected means able to pass a fluid, e.g., a liquid or a gas.

The solenoid valve assembly 64 generally includes a housing 68 and twelve 3-way solenoid valves 70 that are mounted to the housing 68. Each conduit assembly 66 generally includes a tube 61 that interconnects an inlet connector 63 and an outlet connector 65 (see FIG. 6). Each inlet connector 63 is positioned in fluid communication with the solenoid valve assembly 64, and each outlet connector 65 is positioned in fluid communication with a container assembly 15, as described previously.

Referring now to FIGS. 5, 6 and 8-11, the vacuum pump 62 is fluidly connected to an inlet port 72 that is defined on the lower surface of the housing 68 by a tube 74. The inlet port 72 of the housing 68 is fluidly connected to an annular channel 80 (see FIG. 11) defined in the housing 68. The annular channel 80 is fluidly connected to twelve inlet ports 71 that are defined in the housing 68. Each inlet port 71 is fluidly connected to an inlet port of a respective solenoid valve 70. An outlet port of each solenoid valve 70 is fluidly connected to an outlet port 76 of the housing 68. Each outlet port 76 of the housing 68 is radially aligned with a hole 82 disposed in the plate 84 and an inlet connector 63 of a respective conduit assembly 66, such that the outlet port 76 is fluidly connected to that inlet connector 63. The inlet connector 63 is fluidly connected to the inlet connector 65 by the tube 61. The outlet connector 65 is fluidly connected to the interior of a corresponding container assembly 15, thereby exposing the interior of the corresponding container assembly 15 to any vacuum or positive pressure produced by the vacuum pump 62. Physical contact between the underside of the plate 84 of the carrier assembly 21 and the top edge of the container assembly 15 helps to either pressurize the container assembly 15 or create a vacuum condition within the container assembly 15.

The three-way solenoid valves 70 are shown schematically in the figures. Depending upon the setting of the three-way solenoid valve 70, it may pass pressure (positive or negative) to a container assembly 15, prevent the passage of pressure to a container assembly 15, or vent the pressure to the atmosphere. More particularly, in an open configuration, the solenoid valve 70 fluidly connects a corresponding inlet port 71 of the housing 68 with a corresponding outlet port 76 of the housing 68. In a closed position, the solenoid valve 70 does not fluidly connect a corresponding inlet port 71 with a corresponding outlet port 76, thereby preventing the passage of pressure to a corresponding container assembly 15. In the vent position, the solenoid valve 70 vents pressure to the surrounding air, thereby preventing the passage of pressure to a corresponding container assembly 15. As will be described in greater detail hereinafter, the operation of each solenoid valve 70 is controlled by a master controller of the rotary processor 10.

The solenoid valve assembly 64 is mounted to a post 73 that remains fixed in place, while the vertical post 31 rotates and translates (compare FIGS. 4 and 5). Thus, the solenoid valve assembly 64 remains fixed during operation of the rotary processor 10. Because the solenoid valve assembly 64 is fixed in place, each solenoid valve 70 is dedicated to a particular station 14 of the rotary processor 10. In other words, as the sample carriers 20 are moved from one station 14 to another station 14, each solenoid valve 70 continues to deliver pressure to the same station 14 and, therefore, the same container 15, of the processor 10.

The vacuum pump 62 may be configured to deliver either vacuum or positive pressure to the container assemblies 15 depending upon the setting of the vacuum pump 62. The vacuum pump 62 has an inlet port through which air is delivered into the pump and an outlet port through which the air is exhausted out of the pump. In a vacuum mode of the vacuum pump 62, the inlet port of the vacuum pump 62 is fluidly connected to the housing 68 by conduit 74 to deliver vacuum pressure to the container assemblies 15, while the outlet port of the vacuum pump 62 is exposed to atmospheric pressure. In a positive pressure mode of the vacuum pump 62, the outlet port of the vacuum pump 62 is fluidly connected to the housing 68 (via conduit 74 or another conduit that is not shown) to deliver positive pressure to the container assemblies 15, while the inlet port of the vacuum pump 62 is exposed to atmospheric pressure. The conduit 74 may be connected to both the inlet port and the outlet port of the pump 62, and a set of solenoid valves (not shown) may switch to switch the pump between the vacuum mode and the positive pressure mode.

Although not shown, the pressure delivery system 60 may also include a pressure switch or sensor that is configured to detect pressure (i.e., positive or vacuum) that is applied to each container assembly 15 by the vacuum pump 62. The rotary processor 10 is configured to adjust the pressure level applied to each container assembly 15 based upon the pressure levels detected by the pressure switch or sensor. The operator may select a preset pressure level for one or more of the stations of the rotary processor 10 by way of the man-machine interface 18 of the rotary processor 10.

Although not shown, the vacuum system 60 may also include a pressure release valve which is configured to simultaneously release either vacuum pressure or positive pressure at every station of the system.

The vacuum pump 62 may be a commercially available vacuum pump. Although not shown, the vacuum pump 62 may be replaced by a single valve that is connected to a source of pressure (either positive or negative). That valve may be electronically or manually operated. The solenoid valve 70 may be three-way valves, as shown and described. Alternatively, the solenoid valves may be two-way valves, or any discrete, on-off valve. For example, a two-way solenoid valve may provide two of the three options described above for the three-way solenoid valves. The valves 70 may be electronically operated as shown and described, or, alternatively, the valves 70 may be manually operated.

FIG. 12 depicts a simplified electrical schematic diagram of the rotary processor 10. The rotary processor 10 includes a master controller 100. The master controller 100 receives data from a man-machine interface 18 that is provided on the housing assembly 12 of the rotary processor 10. The man-machine interface 18 includes a keyboard and/or a touch screen display that enables an operator to enter parameters for operating every station 14 of the rotary processor 10.

Based upon the parameters entered into the man-machine interface 18 and communicated to the master controller 100, the master controller 100 transmits signals to the motors 25 and 33, the vacuum pump 62, twelve different station controllers 102 (two shown) and twelve different solenoid valves 70 (two shown). The parameters entered by the operator via the man-machine interface 18 for each station 14 may include the following: (i) processing time, (ii) processing temperature, (iii) agitation (yes or no), and (iv) pressure. The pressure settings from which an operator may select are (a) vacuum only, (b) positive pressure only, (c) vacuum and positive pressure, and (d) no positive pressure and no vacuum. The operator may also select a pressure level for the vacuum and positive pressures.

Based upon the power or signals transmitted by the master controller 100, the motors 25 and 33 accomplish translation and rotation of the transport mechanism 16 in order to move the sample carriers 20 from one station 14 to the next station 14 at the predetermined times entered by the operator via the man-machine interface 18.

The signals transmitted by the master controller 100 to the vacuum pump 62 either deactivate the pump 62 or activate the pump 62. The signals transmitted by the master controller 100 to each of the solenoid valves 70 individually control the delivery of pressure to each station 14 while the pump 62 is activated. At any given time, one or more solenoid valves 70 may be open while other solenoid valves 70 are closed.

The twelve station controllers 102 are each responsible for operating a respective station 14. More particularly, based upon a signal transmitted by the master controller 100, each station controller 102 transmits a signal to a connector 44 at a station 14 which passes that signal to the connector 42 of a container assembly 15 that is docked at that station 14. The signal transmitted to the container assembly 15 controls the operation of the heating element of that container assembly 15.

Based upon a signal transmitted by the master controller 100, each station controller 102 transmits a signal to each of the motor-driven magnets 13 to control the agitation in the container assemblies 15. Activating an motor-driven magnet 13 causes a magnetic stirrer bar (not shown) that is located within a container assembly 15 to agitate the contents of that container assembly 15. At any given time, motor-driven magnets 13 at one or more stations 14 may be activated while other motor-driven magnets 13 at other stations 14 are disabled.

Alternatively, the motor-driven magnets 13 may be activated at all times and the operator may control the agitation process by placing a magnetic stirrer bar in only those container assemblies 15 where agitation is desired. As another alternative, the motor-driven magnets 13 and stirrer bars may be omitted in favor of activating the motor 25 to repeatedly translate the tissue carriers 20 up and down to agitate the contents of the container assemblies 15.

FIG. 13 depicts a schematic block diagram of an exemplary method of operating the rotary tissue processor 10. According to the exemplary method, at step 200 twelve container assemblies 15 are manually filled with a particular processing solution (e.g., clearant, paraffin, alcohol, etc.) before they are docked into respective stations 14 of the processor 10. The type of processing solution that is contained within a particular containers 15 dictates the type of station 14 in which that container 15 is docked. For example, a station 14 having a container assembly 15 that is filled with a fixative solution, such as formalin, operates as a fixative station. A station 14 having a container assembly 15 that is filled with a dehydrant solution, such as alcohol, is a dehydrant station. A station 14 having a container assembly 15 that is filled with a clearant solution, such as xylene, is a clearant station. A station 14 having a container assembly 15 that is filled with a plastic or paraffin media operates as a paraffin embedding (or paraffin impregnation) station.

At step 202, once the container assemblies 15 are filled with processing solution, they are individually docked in their respective stations 14 of the rotary processor 10. To accomplish docking of the container assemblies 15, the access door 52 of the fume shield 50 is opened and a first container assembly 15 is docked in a first station 14. The first container assembly 15 is docked in a first station 14 by initially seating the first container assembly 15 in a recess defined by the wall 45 (see FIG. 2) of the first station 14, and rotating the container assembly 15 until the connector 42 of the first container assembly 15 is mated with the connector 44 of the first station 14. The fume shield 50 is then manually rotated in either a clockwise or counterclockwise direction until the access door 52 is aligned with a second station 14. The access door 52 of the fume shield 50 is opened (or remains open) and the second container assembly 15 is docked in the second station 14 by mating the connector 42 of the second container assembly 15 with the connector 44 of the second station 14. This process is repeated until all twelve container assemblies 15 are docked in their respective stations 14. The container assemblies 15 may be docked in any particular order.

At step 204, the operator loads the sample carriers 20 onto the sample carrier hooks 85. To accomplish this task, the operator first raises the vertical post 31 (as shown in FIG. 5), via the man-machine interface 18, to access the sample carrier hooks 85. One or more sample carriers 20 are loaded onto the sample carrier hooks 85. Each sample carrier hook 85 corresponds in position to a particular station 14 of the processor 10. Thus, the operator positions the sample carriers 20 on the hooks 85 that correspond to a specific station 14 of the rotary processor 10.

At step 206, the rotary processor 10 receives operating parameters for processing the tissue samples at each station 14 of the processor 10. In an exemplary embodiment, the master controller 100 of the rotary processor 10 receives the operating parameters. The operating parameters may be received from the operator via the man-machine interface 18 of the rotary processor 10. As noted previously, the particular configuration of a station 14 depends upon the parameters entered by the operator via the man-machine interface 18 for that station and the type of tissue processing solution (e.g., xylene, paraffin, clearant, etc.) contained within the container assembly 15 of that station 14. The parameters entered by the operator via the man-machine interface 18 for each station 14 include the following: (i) processing time, (ii) processing temperature, (iii) agitation (yes or no), and (iv) pressure (i.e., positive pressure only, vacuum pressure only, positive pressure and vacuum pressure, or no positive pressure and no vacuum pressure). The operator may also select a suitable processing program from a list of pre-defined processing programs that are stored in the man-machine interface 18.

Each station 14 may be configured by the operator to perform the same operation for each sample carrier 20 that is loaded onto the system, or, alternatively, each station 14 may be configured to perform different processing operations for the sample carriers 20. In other words, a particular station may process a first sample carrier 20 according to a first processing sequence, and the same station may process a second sample carrier 20 according to a second processing sequence that differs from the first processing sequence.

At step 208, the rotary processor 10 begins to process the samples at each station 14 in accordance with the parameters entered by the operator. In an exemplary embodiment, the master controller 100 directs processing by the rotary processor 10 in accordance with the received parameters. To accomplish step 208, the rotary processor 10 first lowers the vertical post 31 (as shown in FIG. 4), thereby lowering the one or more sample carriers 20 into the processing solution baths of the container assemblies 15. Once each sample carrier 20 is immersed in a container assembly 15 of a respective station 14, each inlet connector 63 is aligned with a housing outlet port 76 of a respective station 14, and each outlet connector 65 is aligned with the container assembly 15 of a respective station 14.

The master controller 100 of the rotary processor 10 then selectively transmits signals to the vacuum pump 62, the solenoid valves 70 and the station controller 102 of each station 14 to control the processing of the sample carriers 20 at each station 14, in accordance with the parameters that were previously entered by the operator. The rotary processor 10 is configured to process the stations 14 simultaneously.

Individualized processing at each station 14 depends upon the parameters entered by the operator. In a station 14 that is parametized as a fixative station, for example, the contents of the container assembly 15 that is docked at that fixative station are heated and agitated. In a station 14 that is parametized as a dehydrant station, the contents of the container assembly 15 that is docked at that dehydrant station are heated, agitated and exposed to vacuum and/or positive pressure. In a station 14 that is parametized as a clearant station, the contents of the container assembly 15 that is docked at that clearant station are agitated. In a station 14 that is parametized as a paraffin embedding (or paraffin impregnation) station, the container assembly 15 that is docked at that embedding (or paraffin impregnation) station are heated, agitated and exposed to vacuum and/or positive pressure. The heating, agitation and pressurization processes are described in greater detailed hereinafter.

If heating of a sample carrier 20 is required at a particular station 14, the station controller 102 of that station 14 transmits either power or a signal to activate the heating element (not shown) of the container assembly 15 of that station 14 at a pre-determined time in order to heat the contents of that container assembly 15 to a pre-determined temperature. If vacuum or pressurization of a container assembly 15 at a particular station 14 is required, the master controller 100 transmits a signal to activate the vacuum pump 62 and transmits a signal to open the solenoid valve 70 of that station 14, thereby exposing that container assembly 15 to either positive or negative pressure. Further details of the pressurization process were described previously. If agitation of a sample carrier 20 is required at a particular station 14, the station controller 102 of that station 14 transmits a signal to activate the magnet 13 of that station 14 at a pre-determined time to agitate the contents of the container assembly 15 of that station 14. Alternatively, every magnet 13 may be activated at all times once processing of the tissue samples has begun.

Once processing of the sample carriers 20 is completed after a pre-determined time has elapsed, each sample carrier 20 is ready to be moved from its respective station 14 to the next station 14. At step 210, the processor 10 moves the sample carriers to the next respective stations 14. To move each sample carrier 20 to the next respective station 14, the master controller 100 first transmits a signal to drive the output shaft of the motor 25 in a clockwise direction. Rotation of the output shaft of the motor 25 in a clockwise direction rotates the drive belt 27 which rotates the threaded shaft 29 which translates the threaded nut 26, the vertical post 31, the plates 83 and 84 and the sample carriers 20 in an upward vertical direction along the axis 'A.' Once the vertical post 31 has completed its upward translation, every sample carrier 20 is lifted out of its container assembly 15 and the inlet connectors 63 are no longer in fluid communication with their respective housing outlet ports 76.

The master controller 100 then transmits a signal to drive the output shaft of the motor 33. Rotation of the output shaft of the motor 33 rotates the drive belt 35 which rotates the vertical post 31, the plates 83 and 84 and the sample carriers 20 about the axis 'A.' The vertical post 31, the plates 83 and 84 and the sample carriers 20 are rotated approximately 30 degrees (i.e., 360 degrees divided by the number of stations) in a clockwise direction about the axis 'A.' Once the vertical post 31 is rotated by 30 degrees, every sample carrier 20 is positioned above the container assembly 15 of the next station 14.

The master controller 100 then transmits a signal to drive the output shaft of the motor 25 in a counterclockwise direction. Rotation of the output shaft of the motor 25 in a counterclockwise direction rotates the drive belt 27, which rotates the threaded shaft 29, which translates the threaded nut 26, the vertical post 31, the plates 83 and 84 and the sample carriers 20 in a downward vertical direction along the axis 'A.' Once the vertical post 31 has completed its downward translation, each sample carrier 20 is immersed in a container assembly 15 of the next station 14, each inlet connector 63 is aligned with a housing outlet port 76 of the next station 14, and each outlet connector 65 is aligned with the container assembly 15 of the next station 14. Following step 210, each sample carrier 20 is ready for further processing at its respective next station 14.

At step 212, each sample carrier 20 is processed at its respective next station 14 in accordance with the parameters entered by the operator. The details provided above for step 208 also apply to step 212. It should be understood that each station is capable of performing the same function as before, or a different function. Following step 212, the process returns to step 210 whereby the sample carriers are transported again to the next respective stations 14 (note arrow leading from step 212 to step 210). Processing of the tissue samples is complete once every sample carrier 20 is processed at every station 14 of the rotary processor 10.

Although this invention has been described with reference to particular embodiments, it will be appreciated that many variations may be resorted to without departing from the spirit and scope of this invention. For example, the number of stations and the functionality of each station may vary from that described herein without departing from the scope and the spirit of the invention. According to this exemplary embodiment, each container assembly 15 is manually filled with the tissue processing solutions (e.g., xylene, paraffin, clearant, etc.) by an operator of the rotary processor, however, the solution may be automatically delivered into the container assembly 15 by a tube that is connected to a source of solution.

What is claimed:

1. A configurable tissue processing system comprising:
   a plurality of configurable tissue processing stations, each station configured to receive one or more tissue samples and selectively configurable to heat, agitate and apply either a positive pressure or a vacuum pressure to the received tissue samples;
   a transport mechanism that is configured to transport the one or more tissue samples between the plurality of configurable tissue processing stations;
   a control unit coupled to the plurality of configurable tissue processing stations and to the transport mechanism, the control unit controlling the transport mechanism to selectively position the one or more tissue samples in the plurality of configurable tissue processing stations, and the control unit configuring each of the plurality of configurable tissue processing stations to heat, agitate and apply either a positive pressure or a vacuum pressure to the received samples; and
   a pressure delivery system that selectively exposes the one or more tissue samples at every tissue processing station to either a source of vacuum or a source of positive pressure;
   wherein the pressure delivery system comprises a plurality of valves that are each fluidly connected to the source of vacuum or positive pressure, wherein each valve is configured to expose the one or more tissue samples to the source of vacuum or positive pressure when the valve is maintained in an open position, and wherein the valve is not configured to expose the one or more tissue samples to the source of vacuum or positive pressure when the valve is maintained in a closed position.

2. The system of claim 1, wherein the pressure delivery system further comprises a plurality of conduits that are each fluidly coupled between one of the plurality of valves and one of the plurality of stations to expose said one of the plurality stations to the source of vacuum or positive pressure while said one of the plurality of valves is maintained in an open position.

3. The system of claim 2, wherein each valve includes an inlet port that is fluidly coupled to the source of vacuum or positive pressure, and an outlet port that is fluidly coupled to one of the plurality of conduits.

4. The system of claim 3, wherein each valve is either a three-way valve or a three-port valve that fluidly connects said one of the plurality of conduits to the source of vacuum, the source of positive pressure or atmosphere.

5. The system of claim 3, wherein an inlet end of each conduit is releasably positioned in fluid communication with an outlet port of one of the plurality of valves and an outlet end of each conduit is releasably positioned in fluid communication with one of the plurality of stations.

6. The system of claim 5, wherein when a tissue sample is docked at the first station of the plurality of stations, the inlet end of a first conduit of the plurality of conduits is positioned in fluid communication with a first valve of the plurality of valves and the outlet end of the first conduit of the plurality of conduits is positioned in fluid communication with the first station of the plurality of stations, and
   wherein when said tissue sample is docked at the second station of the plurality of stations, the inlet end of the first conduit of the plurality of conduits is positioned in fluid communication with a second valve of the plurality of valves and the outlet end of the first conduit of the plurality of conduits is positioned in fluid communication with the second station of the plurality of stations.

7. The system of claim 2, wherein as the transport mechanism transports the tissue samples from a first station of the plurality of stations to a second station of the plurality of stations the plurality of conduits of the pressure delivery system are transported along with the one or more tissue samples while the plurality of valves remain fixed in position.

8. The system of claim 1, wherein each station includes a container for containing the one or more tissue samples.

9. The system of claim 8, wherein each station includes a heating element that is configured to heat the one or more tissue samples that are contained within the container.

10. The system of claim 8 further comprising one or more magnets that is/are configured to spin a magnetic bar positioned within each container to agitate the one or more tissue samples that are contained within the container.

11. The system of claim 8 further comprising a stir bar positioned in at least one of the containers for mixing processing solution that is contained within said at least one of the containers.

12. The system of claim 11 further comprising a magnet for spinning the stir bar to mix the processing solution that is contained within said at least one of the containers.

13. The system of claim 1 further comprising a pressure release valve which is configured to simultaneously release vacuum or positive pressure at every station of the system.

14. A configurable tissue processing system comprising:
   a plurality of configurable tissue processing stations, each station configured to receive one or more tissue samples;
   a transport mechanism that is configured to transport the one or more tissue samples between the plurality of configurable tissue processing stations; and
   a pressure delivery system that selectively and simultaneously exposes the one or more tissue samples at every tissue processing station to either a source of vacuum or a source of positive pressure at every tissue processing station,
   wherein the pressure delivery system comprises a plurality of valves that are each fluidly connected to the source of vacuum or positive pressure.

15. The system of claim 14, wherein the pressure delivery system further comprises a plurality of conduits that are each fluidly coupled between one of the plurality of valves and one of the plurality of stations to expose said one of the plurality stations to either the source of vacuum or the source of positive pressure while said one of the plurality of valves is maintained in an open position.

16. The system of claim 15, wherein each valve includes an inlet port that is fluidly coupled to either the source of vacuum or the source of positive pressure, and an outlet port that is fluidly coupled to one of the plurality of conduits.

17. The system of claim 16, wherein an inlet end of each conduit is releasably positioned in fluid communication with an outlet port of one of the plurality of valves and an outlet end of each conduit is releasably positioned in fluid communication with one of the plurality of stations.

18. The system of claim 17, wherein when a tissue sample is docked at the first station of the plurality of stations, the inlet end of a first conduit of the plurality of conduits is positioned in fluid communication with a first valve of the plurality of valves and the outlet end of the first conduit of the plurality of conduits is positioned in fluid communication with the first station of the plurality of stations, and
   wherein when said tissue sample is docked at the second station of the plurality of stations, the inlet end of the first conduit of the plurality of conduits is positioned in fluid communication with a second valve of the plurality of valves and the outlet end of the first conduit of the plurality of conduits is positioned in fluid communication with the second station of the plurality of stations.

19. The system of claim 15, wherein as the transport mechanism transports the tissue samples from a first station of the plurality of stations to a second station of the plurality of stations the plurality of conduits of the pressure delivery system are transported along with the one or more tissue samples while the plurality of valves remain fixed in position.

20. The system of claim 14, wherein the pressure delivery system comprises a pressure switch which is configured to detect a level of pressure at one of the processing stations, wherein the system is configured to adjust the level of pressure at said one of the processing stations based upon the detected level of pressure.

21. The system of claim 14 further comprising a fume shield that at least partially encloses the configurable tissue processing system.

22. The system of claim 14 further comprising an exhaust fan for exhausting fumes within an interior region of the configurable tissue processing system.

* * * * *